US012329556B2

(12) United States Patent
Patriciu et al.

(10) Patent No.: US 12,329,556 B2
(45) Date of Patent: Jun. 17, 2025

(54) 3-D MEASUREMENTS GRID TOOL FOR X-RAY IMAGES

(71) Applicant: KONINKLIJKE PHILIPS N.V., Eindhoven (NL)

(72) Inventors: Alexandru Patriciu, Belmont, MA (US); Alyssa Torjesen, Charlestown, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 409 days.

(21) Appl. No.: 17/912,836

(22) PCT Filed: Mar. 15, 2021

(86) PCT No.: PCT/EP2021/056537
§ 371 (c)(1),
(2) Date: Sep. 19, 2022

(87) PCT Pub. No.: WO2021/185764
PCT Pub. Date: Sep. 23, 2021

(65) Prior Publication Data
US 2023/0147764 A1  May 11, 2023

Related U.S. Application Data

(60) Provisional application No. 62/992,189, filed on Mar. 20, 2020.

(51) Int. Cl.
*A61B 6/00* (2024.01)
*A61B 6/46* (2024.01)

(52) U.S. Cl.
CPC ............ *A61B 6/4441* (2013.01); *A61B 6/461* (2013.01); *A61B 6/5229* (2013.01); *A61B 6/52* (2013.01)

(58) Field of Classification Search
CPC ..... A61B 6/5229; A61B 6/4441; A61B 6/461; A61B 6/52; A61B 6/032; A61B 6/4035;
(Continued)

(56) References Cited

U.S. PATENT DOCUMENTS

2016/0015350 A1* 1/2016 Chang ................... A61B 6/032
                                                              250/362
2016/0324580 A1* 11/2016 Esterberg ............... A61B 34/10
(Continued)

FOREIGN PATENT DOCUMENTS

| CN | 101958006 A | 1/2011 |
| CN | 109602428 A | 4/2019 |

OTHER PUBLICATIONS

International Search Report and Written Opinion of PCT/EP2021//056537, dated Jun. 18, 2021.
(Continued)

*Primary Examiner* — Irakli Kiknadze (57) ABSTRACT

Method of calculating a scaled virtual grid for x-ray projection images, comprising providing at least a first and a second co-registered x-ray projection image $I_j$–$j$=1, 2, . . . of a desired anatomy of a patient (step S1), defining two points $P_1$ and $P_2$ of the desired anatomy in 3-D space and determining 3-D coordinates of the two points $P_1$ and $P_2$ thereby using the x-ray projection images (step S2), calculating the scaled virtual grid based on the determined 3-D coordinates of the two points $P_1$ and $P_2$ (step S3), and projecting and displaying the calculated grid to a user on at least one of the first and the second co-registered x-ray projection image (step S4).

20 Claims, 4 Drawing Sheets

(58) Field of Classification Search
CPC ... A61B 6/5211; A61B 6/5282; A61B 6/4291; A61B 6/06; A61B 6/483; A61B 6/4085; A61B 6/5235; A61B 6/5205; A61B 6/4476; A61B 2576/00; A61B 34/10; A61B 34/20; A61B 5/055; A61B 2034/107; A61B 2034/2063; A61B 2034/2055; A61B 90/98; A61B 2090/309; A61B 2034/2051; A61B 2090/372; A61B 2090/373; A61B 2090/502; A61B 2034/2048; A61B 2560/0487; A61B 2090/371; A61B 2017/00207; A61B 2034/2072; A61B 2034/2065; A61B 2090/365; A61B 6/56; A61B 6/5258; A61B 6/466; A61B 34/30; A61B 90/37; A61B 17/846; A61B 34/25; A61B 2034/256; A61B 2090/376; A61B 2017/00203; A61B 2017/00216; A61B 2090/3966; A61B 2560/0223; A61B 2090/367; A61B 6/486; A61B 6/5217; A61B 6/5223; A61B 6/582; A61B 90/00; A61B 90/06; A61B 2090/061; A61B 6/4405; A61B 6/0407; A61B 6/584; A61B 90/39; G06T 15/20; G06T 5/00; G06T 11/005; G06T 7/0012; G06T 5/70; G06T 11/20; G06T 2207/10081; G06T 2211/424; G06T 2207/30004; G06T 5/73; G06T 11/003; G06T 11/006; G06T 11/00; G06T 3/153; G06T 2207/30168; G06T 2207/10116; G06T 5/006; G06T 7/75; G06T 2207/10124; G06T 2207/30012; G06T 2207/30244; G06T 11/008; G06T 2211/421; G06T 5/80; G06T 2207/20048; G01N 23/046; G01N 2223/401; G09B 23/286; G16H 50/20; G16H 50/30; G21K 1/10; G21K 5/04; G01B 15/02; G06F 3/011; A61N 5/1049; A61N 2005/1061; A61N 5/1067; A61F 2/461; A61F 2/4607; G03B 42/02

USPC .............................................................. 378/4

See application file for complete search history.

(56) References Cited

U.S. PATENT DOCUMENTS

| | | | |
|---|---|---|---|
| 2018/0268573 A1* | 9/2018 | Fukuda | G01B 15/02 |
| 2018/0325485 A1* | 11/2018 | Maslowski | G06T 5/00 |
| 2019/0122330 A1 | 4/2019 | Saget | |
| 2019/0320995 A1 | 10/2019 | Amire | |
| 2021/0012492 A1 | 1/2021 | Karade | |
| 2021/0256760 A1* | 8/2021 | Tomaru | G06T 15/20 |

OTHER PUBLICATIONS

Sitz, Alexander et al "Determining the orientation angle of directional leads for deep brain stimulation using computed tomography and digital x-ray imaging: A phantom study", Medical Physics, vol. 44, No. 9, Sep. 2017.

Hunsche, S. et al "Determining the Rotational Orientation of Directional Deep Brain Stimulation Leads Employing Flat-Panel Computed Tomography", Oper Neurosurgery, vol. 16, No. 4, 2019, pp. 465-470.

* cited by examiner

3-D MEASUREMENTS GRID TOOL FOR X-RAY IMAGES

CROSS-REFERENCE TO PRIOR APPLICATIONS

This application is the U.S. National Phase application under 35 U.S.C. § 371 of International Application No. PCT/EP2021/056537, filed on Mar. 15, 2021, which claims the benefit of U.S. Provisional Patent Application No. 62/992,189, filed Mar. 20, 2020. These applications are hereby incorporated by reference herein.

FIELD OF THE INVENTION

The present invention relates to a method of calculating a scaled virtual grid for x-ray projection images, a device for calculating such a scaled virtual grid for x-ray projection images, a system for calculating such a scaled virtual grid for x-ray projection images and a program element for such a method.

BACKGROUND OF THE INVENTION

Mobile X-ray fluoroscopy for imaging of objects is known in the state of the art as well as widely used in various fields such as e.g. orthopedics, trauma, vascular and spine. Due to their design mobile x-ray fluoroscopies are characterized compared to fixed x-ray systems by a small footprint, a high maneuverability and reduced costs. Depending on the information required of the object sometimes several pictures have to be taken and analyzed. Physicians use these pictures as basis for their preparation of surgical procedures to get size information about proper implants, e.g. screws. Therefore normally an object of known size is overlapped over a desired anatomy of the patient during X-ray imaging. In case the object is not plane parallel to the detector or if area of the anatomy lays not in the plane of the object, the estimated distances are less reliable and the measurement lacks of accuracy.

For the inventors of the present invention, it has now become apparent that there is a need for improving the analysis of x-ray images of such mobile x-ray fluoroscopies. In particular there is a need to increase the efficiency of the geometrical information gained by the analysis of x-ray images of such a mobile x-ray fluoroscopy.

SUMMARY OF THE INVENTION

It is therefore the task of the present invention, to provide a method and a system, which enable an efficient analysis of x-ray images of, for example, such a mobile x-ray fluoroscopy. This task and other tasks, which are further mentioned when reading the following description or can be recognized by the skilled person, are solved by the subject-matter of the independent claims. Further embodiments and advantages of the invention are incorporated in the dependent claims.

The described embodiments similarly pertain to the method, the calculation device, the system and the computer program element and the computer-readable medium. Synergetic effects may arise from different combinations of the embodiments although they might not be described in detail.

Further on, it shall be noted that all embodiments of the present invention concerning a method, might be carried out with the order of the steps as described, nevertheless this has not to be the only and essential order of the steps of the method. The herein presented methods can be carried out with another order of the disclosed steps without departing from the respective method embodiment, unless explicitly mentioned to the contrary hereinafter.

Technical terms are used by their common sense. If a specific meaning is conveyed to certain terms, definitions of terms will be given in the following in the context of which the terms are used.

According to a first aspect of the present invention, a method for calculating a scaled virtual grid for x-ray projection images is provided. The method comprises providing at least a first and a second co-registered x-ray projection image $I_j$, j=1, 2, . . . of a desired anatomy of a patient (step S1), defining two points $P_1$ and $P_2$ of the desired anatomy in 3-D space and determining 3-D coordinates of the two points $P_1$ and $P_2$ thereby using the x-ray projection images (step S2), calculating the scaled virtual grid based on the determined 3-D coordinates of the two points $P_1$ and $P_2$ (step S3), and projecting and displaying the calculated grid to a user on an x-ray projection image, preferably at least one of the first and the second co-registered x-ray projection image (step S4).

The term "scaled virtual grid" is to be understood broadly in the context of the present invention and comprises rectangular and distorted grids with a scale. The term "scale" is also to be understood as a metric of the virtual grid and allows a user/viewer to derive directly measurement values, such as distances, from the x-ray images of the desired anatomy imaged by the at least two projection images. Hence, there is no need for the viewer to estimate a distance in the x-ray image, which implies an increase of the analysis accuracy. Alternatively, the analysis of the scale can also carried out by an algorithm. Also a combination of determining measurement values by the user and by an algorithm are of course possible. It should be noted that determining or deriving measurement values particularly comprises determining or deriving length or distance measurement values. Further details and embodiments of the scaled virtual grid used in the present invention will be explained hereinafter in the context of embodiments and e.g. in the detailed descriptions of the embodiments depicted in FIGS. 5 and 6.

Co-registration of images, particularly of x-ray projection images, is state of the art and is widely used in image acquisition and evaluation. The provision of such co-registered images can comprise the use of co-registered x-ray projection images of external sources, like e.g. medical data bases, other imaging devices etc., as well as self-executed co-registration by means of an algorithm, and/or by the system carrying out the method present herein. Further descriptions of the provision of co-registered x-ray projection images will be explained hereinafter in the context of particular embodiments and e.g. the detailed description of the embodiment shown in FIG. 3.

As is apparent to the skilled reader, image registration is the process of transforming different images/sets of data into one coordinate system. The images/data can be multiple photographs and/or data from different sensors, different times or different viewpoints. It is used in computer vision, medical imaging and in compiling and analyzing images and data from satellites. Registration is necessary in order to be able to compare or integrate the images/data obtained from these different measurements. Thus, co-registered x-ray projection images as used herein, are images which have been transformed into one coordinate system.

The desired anatomy object to be imaged can have any geometry. The definition of the points $P_1$ and $P_2$ and the determination of their 3-D-coordinates can be carried out by the user itself, who is interested in the analysis of the desired object's anatomy, or alternatively by or in combination with an algorithm. Such an algorithm may use patient data and/or an anatomy data base to define the two points $P_1$ and $P_2$ and the determination of their 3-D-coordinates. The user may e.g. provide a user input such that the algorithm automatically identifies the Femur Head in the first image, i.e. thus determining automatically $P_1$ and its 3D coordinates, as well as $P_2$ with respect to the second image.

Speaking generally, the knowledge of the 3-D coordinates enables an exact determination of lengths/distances in the x-ray projection images and not only distance between the two points $P_1$ and $P_2$. Further descriptions of possible ways of defining the two points $P_1$ and $P_2$ will be provided hereinafter in the context of particular, non-limiting embodiments and e.g. the detailed description of the embodiment of FIG. 4.

As will become apparent from the detailed description hereinafter, in one embodiment three points $P_1$, $P_2$ and $P_3$ are defined and their 3D coordinates are determined for calculating the grid.

Moreover, the calculation of the scaled virtual grid can be carried out by various mathematical methods, as will become apparent from the explanations hereinafter in the description of the particular embodiments. In examples, control points ci and cross lines dij can be calculated in various different manners for determining the scaled virtual grid.

Projecting and displaying the calculated grid to a user on at least one of the first and the second co-registered x-ray projection image can be carried out on one or more/various displays, e.g. using an HMI of a CT, and/or static screens and portable smart glasses using Augmented Reality technologies.

This aspect of the present invention is based on the insight of the inventors that the use of objects, which are placed on the desired anatomy during CT-imaging only provides exact measurement data for regions, which lay parallel in the plane of object of known size, wherein the object of known size also has to lay in a plane parallel to the x-ray detector. Hence, every measurement of a distance outside of the plane of the object of known size, wherein the object of known size lays in a plane parallel to the x-ray detector, leads to an unavoidable inaccuracy. These disadvantages is overcome by the present invention. For example, in an especially preferred embodiment of the invention it is possible to measure the distances in x-ray projection images without the use of an additional object of known size for any perspective of the anatomy. The distances in regions of interest to be measured can lay outside a plane parallel to the detector without losing measurement accuracy. Hence, with the use of the grid calculated according to the present invention, the physician can always derive reliable measurement values from the x-ray projection image without an explicit calibration step.

It should be noted that in the context of the present invention the following index convention is used: j represent the image index; i represents reference point index; m represents the control point index on cross line ij. This will become apparent from the following description.

According to an exemplary embodiment, the step of calculating the scaled virtual grid (step S3) comprises: calculating at least two control points $c_i$; i=1, 2, . . . on a line connecting the defined points $P_1$ and $P_2$ (step S3a); calculating for each co-registered image cross lines $d_{ij}$; i=1, 2, . . . ; j=1, 2, . . . (step S3b), wherein each cross line $d_{ij}$ crosses the line connecting the defined points $P_1$ and $P_2$ at control point ci, wherein each cross line $d_{ij}$ is parallel with a detector, with which image $I_j$ was captured, and preferably each cross line $d_{ij}$ is perpendicular to the line connecting the defined two points $P_1$ and $P_2$.

In a preferred embodiment the step of calculating on each cross line $d_{ij}$ control points $k_{ijm}$ (S3c), wherein the control points $k_{ijm}$ define the scaled virtual grid for each image $I_j$.

With each cross lines $d_{ij}$ being parallel with the detector that was generating the corresponding image $I_j$, the scale of the grid is equidistant and does not change the magnification. Further detailed embodiments that build on this way of calculating the grid can be gathered e.g. from the particular embodiment explained in the context of FIGS. 5 and 6.

Alternatively, the grid can also be defined with three selected points $P_1$, $P_2$ and $P_3$, which define a plane, in which the cross lines $d_{ij}$ lie. The cross lines $d_{ij}$ are perpendicular to the line connecting the defined points $P_1$ and $P_2$, but not parallel to the detector. This can be an advantage if your region of interest is located in special plane of the object.

In other words, another way to define the grid is to define/select a third anatomical point $P_3$ in the two x-ray images. $P_3$ together with $P_1$ and $P_2$ define a plane. Then we one use steps S1-S3a, as has been explained in detail hereinbefore and will be elucidated even more hereinafter, to define $c_i$. Then one can uniquely build cross lines $d_{ij}$ in the plane defined by the three points $P_1$, $P_2$ and $P_3$. Such a $d_{ij}$ crossline is perpendicular on $P_1P_2$ line, but it is not parallel anymore with the detectors, as was the case in the embodiment described before. In this approach, the grid is calibrated and attached to the plane defined by $P_1P_2P_3$, as is clear to person skilled in the art from this disclosure.

According to another exemplary embodiment of the invention the method comprises the steps of projecting and displaying the scaled virtual grid, which is defined by control points $k_{i1m}$ on the first co-registered x-ray projection image $I_1$ to the user, and projecting and displaying the scaled virtual grid, which is defined by control points $k_{i2m}$ on the second co-registered x-ray projection image $I_2$ to the user.

In other words, in this embodiment the calculated grid is laid over the first and second co-registered x-ray projection images $I_1$ and $I_2$ to be used by the user on a display. Hence, the user/viewer has the scale information for the analysis of the region of interest in both co-registered x-ray projection images $I_1$ and $I_2$.

According to another exemplary embodiment of the invention, the method comprises calculating the distance in 3-D space between the two points $P_1$ and $P_2$, and using the calculated distance to determine the distance between at least two control points $k_{ijm}$.

The scale of the grid is calculated in cross direction and in longitudinal direction with the determination of the distances between all control points $k_{ijm}$. The distances between two neighboring control points $k_{ijm}$ can have any values, but preferably they have equidistant values. It may be the case that humans can recognize or analyze easier grids with an equidistant grid size.

According to another exemplary embodiment of the invention, the method comprises displaying the determined distance between the at least two control points $k_{ijm}$ together with the control points $k_{ijm}$ on the image Ij to the user.

The distances between the control points $k_{ijm}$ may be understood to represent the grid and serve the viewer as scale and/or metric. Further descriptions of displaying the determined distance between the control points $k_{ijm}$ together with the control points $k_{ijm}$ on the image $I_j$ to the user can easily gathered from the embodiment described and shown with FIG. 5 hereinafter.

According to another exemplary embodiment of the invention, the first and second co-registered x-ray projection images show the desired anatomy of the patient from different perspectives.

The different perspectives enable various information of the region of interest, e.g. information, which is hidden in one perspective, is visible in another perspective. The different perspectives are the basis for the necessary alignment of the points $P_1$ or $P_2$ in the co-registered x-ray projection images, which serves further the determination of the 3-D coordinates of the points $P_1$ and $P_2$ in space. Further descriptions of the different perspectives can be found in embodiments hereafter and in the detailed description of FIG. 4.

According to another exemplary embodiment of the invention, the method comprises localizing an x-ray imaging device in six degrees of freedom, wherein the provided first and second co-registered x-ray projection images were generated with said x-ray imaging device.

The localizing or localization of the x-ray imaging device is a requirement for the co-registration of the x-ray projection images, which are further processed for generating the virtual grid. X-ray imaging devices are well known in the state of the art, and examples will be mentioned hereinafter briefly. In this embodiment the x-ray imaging device comprises a source and corresponding a detector, which can move in dependence to each other in 6 degrees of freedom. This means that there is a fixed geometric constraint between the source and the detector. The anatomy object is placed between the x-ray source and the x-ray detector. Hence, it is possible to align the images of the x-ray imaging device with the information of the position of the x-ray imaging device comprising 6 degrees of freedom.

According to another exemplary embodiment of the invention, the localization is carried out using a ripple marker, using optical tracking of the x-ray imaging device, using internal encoders of the x-ray imaging device, and/or using other image-based markers.

Hence, there are different opportunities for the same aim, i.e. the localization of the x-ray imaging devices in space, which can be used single or in combination for the sake of protection through redundancies.

In another exemplary embodiment of the method the step of defining two points P1 and P2 of the desired anatomy in 3-D space (step S2) comprises identifying a first landmark of the desired anatomy in the first x-ray projection image (step S2a), determining a first line on which the first landmark lies between an x-ray source and an x-ray detector that were used for generating the first x-ray projection image (step S2b), identifying a second landmark of the desired anatomy in the second x-ray projection image (step S2c), determining a second line on which the second landmark lies between the x-ray source and the x-ray detector that were used for generating the second x-ray projection image (step S2d), and calculating 3-D coordinates of an intersection of the determined first and second lines (step S2e), wherein the calculated 3-D coordinates define point $P_1$ in 3-D space; identifying a third landmark of the desired anatomy in the first x-ray projection image (step S2f), determining a third line on which the third landmark lies between the x-ray source and the x-ray detector that were used for generating the first x-ray projection image (step S2g), identifying a fourth landmark of the desired anatomy in the second x-ray projection image (step S2h), determining a fourth line on which the fourth landmark lies between the x-ray source and the x-ray detector that were used for generating the second x-ray projection image (step S2i), and calculating 3-D coordinates of an intersection of the determined third and fourth lines (step S2j), wherein the calculated 3-D coordinates define point $P_2$ in 3-D space.

It should be noted that said steps of this embodiment, particularly the steps of identifying said landmarks and determining said lines can be carried out manually, e.g. based on a user input via e.g. a HMI, but can also be carried out purely automatically using e.g. image processing algorithms. Of course, also a combination of both alternative ways can be used without departing from the preset invention. Moreover, a particularly detailed embodiment of how the two points $P_1$ and $P_2$ of the desired anatomy in 3-D space can be defined using the identification of said landmarks and the determination of said lines can be gathered from e.g. FIG. 4 and the corresponding description.

In another exemplary embodiment, the method comprises projecting the determined first line onto the second x-ray projection image, and/or projecting the determined third line onto the second x-ray projection image.

It shall be mentioned, that the step of defining the two points $P_1$ and $P_2$ is not limited to lines as geometric tools, as is clear to the skilled reader. Also other geometric forms e.g. circles, triangles etc. are possible to carry out the method. Further explanation of defining the points can be found in the detailed description of FIG. 4, in which a projection of the determined first line onto the second x-ray projection image is shown.

In another exemplary embodiment the projection of the determined first and/or third line is used as a constraint, e.g. on a Human Machine Interface (HMI), which constraint constrains user input possibilities for identifying a landmark in the second x-ray projection image, e.g. on said HMI.

The constraint limit may limit the solution space for an alignment of e.g. $P_1$ in the first and second x-ray projection image, while defining or identifying $P_2$. Hence, the constraint assists the user of HMI and reduces the possible error rate or increases the accuracy of the scale of the grid. As mentioned above, it is also possible to automate the definition of the points $P_1$ and $P_2$ by an algorithm based on patient data or anatomical database, which does not require a user input via a HMI.

According to another exemplary embodiment, the method comprises the step of generating the first and second x-ray projection images with an x-ray imaging device, preferably with a mobile C-arm CT, comprising an x-ray source and an x-ray detector.

Mobile C-arm CT are well known from the state of the art and allow the user to easily generate images of different perspectives of the desired object. Further explanations about generating the first and second x-ray projection image can be found in the detailed description of the embodiment shown in FIG. 3.

According to further aspect of the present invention a device for calculating a scaled virtual grid for x-ray projection images is presented. The device comprises a calculation unit configured for: receiving at least a first and a second co-registered x-ray projection image $I_j$ of a desired anatomy of a patient, calculating two points $P_1$ and $P_2$ in the x-ray projection images and in the desired anatomy thereby determining 3-D coordinates of the two points $P_1$ and $P_2$, calculating the scaled virtual grid based on the determined 3-D coordinates of the two points $P_1$ and $P_2$, and causing a projection and a displaying of the calculated grid to a user on at least one of the first and the second co-registered x-ray projection image.

Such a device may be e.g. a processor that can be part of an x-ray imaging device, such as a mobile C-arm CT, comprising also an x-ray source and an x-ray detector. But said device for calculating a scaled virtual grid for x-ray projection images may also be a separate component that receives as an input the images and delivers as an output the calculated grid. Moreover, the calculation device may itself project and display the calculated grid to the user on at least one, preferably both, co-registered x-ray projection images. Alternatively, the calculation device may generate e.g. one or more control signals that cause another device, like e.g. a projector or a display to carry out the projection and the displaying of the calculated grid to the user on one or both or more co-registered x-ray projection images.

A further aspect of the present invention relates to a system for calculating a scaled virtual grid for x-ray projection images comprising a device for a scaled virtual grid for x-ray projection images as mentioned hereinbefore. It also comprises a Human Machine Interface (HMI) configured for displaying the received first and a second co-registered x-ray projection images and configured for receiving input signals from the user e.g. for identifying landmarks in the displayed images of the desired anatomy.

According to another exemplary embodiment, the system comprises an x-ray imaging device, preferably a mobile C-arm CT, comprising an x-ray source and an x-ray detector for generating the x-ray projection images.

It should be noted that the afore mentioned parts of the system can be arranged centrally or decentralized to each other. Centrally means in that all parts of the system are at least in a wired connection and decentralized means that the parts can be elsewhere and communicate with each other via a wireless network.

A further aspect of the present invention relates to a program element, which, when run on a processor or computer, is configured to carry out the method for calculating a scaled virtual grid for x-ray projection images as described herein.

The program element may be part of a computer program, but it can also be an entire program by itself. For example, the program element may be used to update an already existing computer program to get to the present invention.

A further aspect of the present invention relates to a computer readable medium, on which such a program element, as described before, is stored.

The computer readable medium may be seen as a storage medium, such as for example, a USB stick, a CD, a DVD, a data storage device, a hard disk, or any other medium on which a program element as described above can be stored.

BRIEF DESCRIPTION OF THE DRAWINGS

In the following, the disclosure is described exemplarily with reference to the enclosed figures, in which.

Notably, the figures are merely schematic representations and serve only to illustrate embodiments of the present disclosure. Identical or equivalent elements are in principle provided with the same reference signs.

DETAILED DESCRIPTION OF EMBODIMENTS

Figure 1:
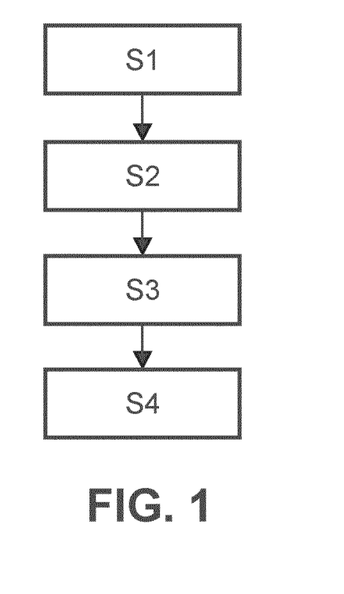
FIG. 1 shows a flow diagram of the method for calculating a scaled virtual grid for x-ray projection images according to an embodiment.

FIG. 1 shows a flow diagram of the method for calculating a scaled virtual grid for x-ray projection images according to an embodiment of the present invention. The steps comprise the provision of at least a first and a second co-registered x-ray projection image of a desired anatomy of a patient (step S1), defining two points $P_1$ and $P_2$ of the desired anatomy in 3-D space and determining 3-D coordinates of the two points $P_1$ and $P_2$ thereby using the x-ray projection images (step S2), calculating the scaled virtual grid based on the determined 3-D coordinates of the two points $P_1$ and $P_2$ (step S3), and projecting and displaying the calculated grid to a user on at least one of the first and the second co-registered x-ray projection image (step S4).

In other words, in step S1 at least two co-registered x-ray projections of a desired anatomy from different perspectives are be provided and further used for the calculation the scaled grid. The co-registered x-ray projections serve as data basis for the following steps. The different perspectives of the co-registered x-ray projections are necessary, for the second step S2, wherein two points are defined respectively selected in the region of interest in the co-registered x-ray projection image. For determining the 3-D coordinates of these two points an alignment of each selected point with the corresponding position in the other co-registered x-ray projection image is carried out. With this position information of each point in both co-registered x-ray projection images it is possible to determine the 3-D coordinates of each point in the 3-D space of the desired anatomy. These 3-D coordinates of the two points serve as base for a scale grid of the anatomy, which is designed in step S3. In the last step S3 the designed scale grid is projected on co-registered x-ray projections, which means it is overlaid on the co-registered x-ray projections. Hence, there is a calibrated scale grid overlaid on both co-registered x-ray projections, which is displayed to a user.

Figure 2:
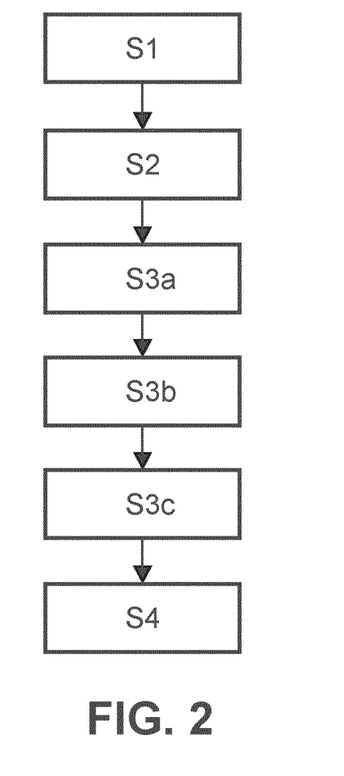
FIG. 2 shows another embodiment of the method for calculating a scaled virtual grid by means of a flow diagram.

Note that the calculation of the scaled virtual grid can be carried out by various mathematical methods, as will be elucidated with two embodiments explained in the context of FIG. 2. Moreover, projecting and displaying the calculated grid to a user on at least one of the first and the second co-registered x-ray projection image can be carried out on one or more/various displays, e.g. using an HMI of a CT, and/or static screens and portable smart glasses using Augmented Reality technologies.

This method is based on the insight of the inventors that the use of objects, which are placed on the desired anatomy during CT-imaging only provides exact measurement data for regions, which lay parallel in the plane of object of known size, wherein the object of known size also has to lay in a plane parallel to the x-ray detector. Hence, every measurement of a distance outside of the plane of the object of known size, wherein the object of known size lays in a plane parallel to the x-ray detector, leads to an unavoidable inaccuracy. These disadvantages is overcome by the method of FIG. 2. For example, in an especially preferred embodiment of the invention it is possible to measure the distances in x-ray projection images without the use of an additional object of known size for any perspective of the anatomy. The distances in regions of interest to be measured can lay outside a plane parallel to the detector without losing measurement accuracy. Hence, with the use of the grid calculated according to the method of FIG. 2, the physician can always derive reliable measurement values from the x-ray projection image without an explicit calibration step.

FIG. 2 shows another embodiment of the method for calculating a scaled virtual grid by means of a flow diagram. In this embodiment, step S3 is further divided in the following sub-steps: calculating at least two control points $c_i$, i=1, 2, . . . on a line connecting the defined points $P_1$ and $P_2$ (step S3a); calculating for each co-registered image cross lines $d_{ij}$; i=1, 2, . . . ; j=1, 2, . . . (step S3b), wherein each cross line $d_{ij}$ crosses the line connecting the defined points $P_1$ and $P_2$ at control point $c_i$, wherein each cross line $d_{ij}$ is parallel with a detector, with which image $I_j$ was captured, and preferably each cross line $d_{ij}$ is perpendicular to the line connecting the defined two points $P_1$ and $P_2$ and calculating on each cross line $d_{ij}$ control points $k_{ijm}$ (S3c), wherein the control points $k_{ijm}$ define the scaled virtual grid for each image $I_j$.

In other words, a line is drawn between the two points $P_1$ and $P_2$, wherein the line serves a center line in the grid. The line is further divided in part sections, defined by the point $c_i$ (step S3a). These part sections define the grid size in one direction. The calculated crosslines $d_{ij}$ run through the points $c_i$ and are perpendicular to the center line and parallel to each other (step S3b). Each cross line $d_{ij}$ shows calculated points $k_{ijm}$ (step S3c). These points define the mesh size in the second direction. As a result, you gain the calibrated scale grid for x-ray projection images for the desired anatomy.

Alternatively, the grid can also be defined with three selected points $P_1$, $P_2$ and $P_3$, which define a plane, in which the cross lines $d_{ij}$ lie. The cross lines di are perpendicular to the line connecting the defined points $P_1$ and $P_2$, but not parallel to the detector. This can be an advantage if your region of interest is located in special plane of the object. In other words, another way to define the grid is to define/select a third anatomical point $P_3$ in the two x-ray images. $P_3$ together with $P_1$ and $P_2$ define a plane. Then we one use steps S1-S3a, as has been explained in detail hereinbefore and will be elucidated even more hereinafter, to define $c_i$. Then one can uniquely build cross lines $d_{ij}$ in the plane defined by the three points $P_1$, $P_2$ and $P_3$. Such a $d_{ij}$ crossline is perpendicular on $P_1P_2$, but it is not parallel anymore with the detectors, as was the case in the embodiment described before. In this approach, the grid is calibrated and attached to the plane defined by $P_1P_2P_3$, as is clear to person skilled in the art from this disclosure.

Figure 3:
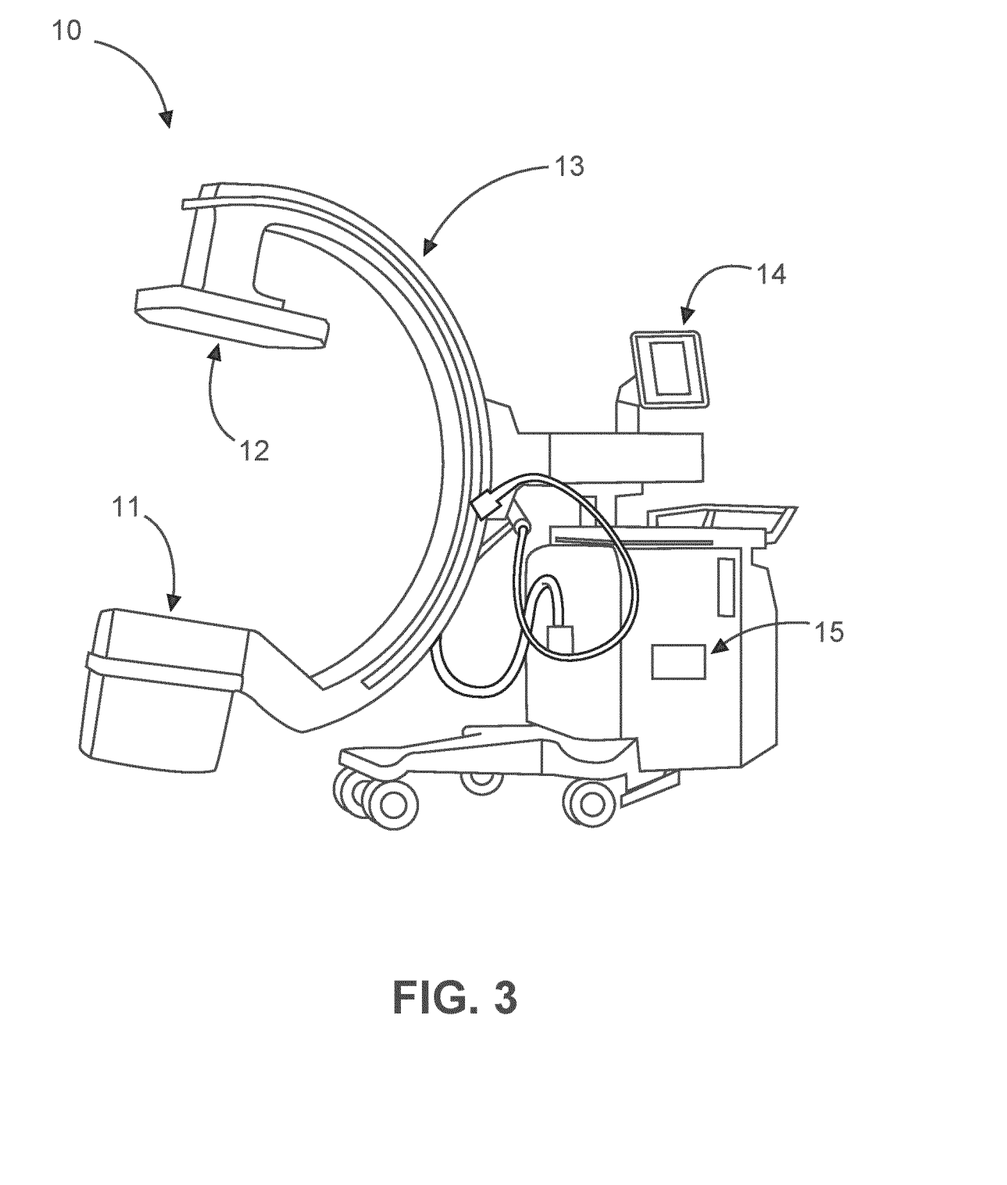
FIG. 3 shows a schematic view of a system for calculating a scaled virtual grid for x-ray projection images according to an embodiment.

FIG. 3 shows a schematic view of the system 10 for calculating a scaled virtual grid for x-ray projection images according to the preferred embodiment. The system 10 comprises a mobile C-arm CT, comprising an x-ray source 11 and an x-ray detector 12, which are mounted on C-arm 13. The C-arm 13 can move in six directions, i.e. three translatory directions and three rotatory directions. The desired anatomy is positioned in the center of the C-arm such that the x-ray source 11 can emit radiation on the desired anatomy and the corresponding x-ray detector 12 can detect the emitted radiation, which is influenced by the desired anatomy. In this way the x-ray projection images of the desired anatomy are acquired. With the information of the position of the C-arm 13 the x-ray projection images can be co-registered through various calculation methods (not shown). The information of the position respectively the six space coordinates of the C-arm are acquired by so called ripple marker (not shown). The system further comprises a Human Machine Interface (HMI) 14 configured for displaying the received first and a second co-registered x-ray projection images and configured for receiving input signals from the user for identifying landmarks in the displayed images of the desired anatomy. The nature and use of the landmarks will become apparent from the description of the embodiment shown in FIG. 4.

The system further comprises a calculation unit 15, which is configured for receiving at least a first and a second co-registered x-ray projection image $I_j$ of a desired anatomy of a patient, calculating two points $P_1$ and $P_2$ in the x-ray projection images and in the desired anatomy thereby determining 3-D coordinates of the two points $P_1$ and $P_2$. The calculation unit can calculate the scaled virtual grid based on the determined 3-D coordinates of the two points $P_1$ and $P_2$, and causes projection and a displaying of the calculated grid to a user on at least one of the first and the second co-registered x-ray projection image. In other words the calculation unit 15 is responsible for all steps of the calculation of the grid and the control of the projection and displaying the grid to a user.

Figure 4:
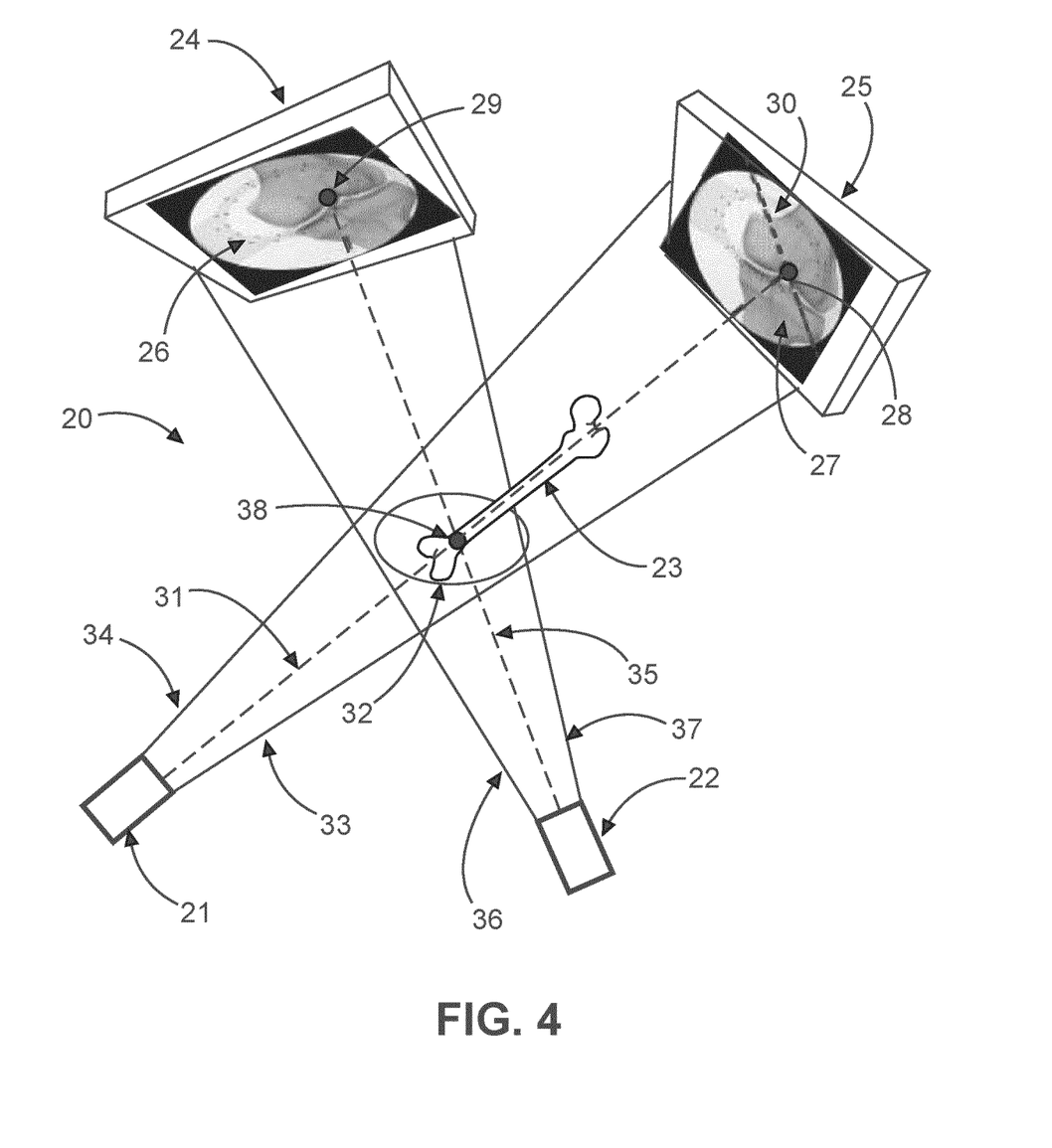
FIG. 4 schematically shows how the definition of one point $P_1$ of the desired anatomy in 3-D space and the determination of the 3-D coordinates of the point $P_1$ are carried out in an exemplary embodiment.

FIG. 4 shows a schematic view 20 of defining one point 29 of the desired anatomy 23 in 3-D space and determining 3-D coordinates of the point 29. Identifying a first landmark 29 of the desired anatomy 23 in the first x-ray projection image 26 (step S2a), determining a first line 35 on which the first landmark 29 lies between an x-ray source 22 and an x-ray detector 24 that were used for generating the first x-ray projection image 26 (step S2b), identifying a second landmark 28 of the desired anatomy 23 in the second x-ray projection image 27 (step S2c), determining a second line 31 on which the second landmark 28 lies between the x-ray source 21 and the x-ray detector 25 that were used for generating the second x-ray projection image 27 (step S2d), and calculating 3-D coordinates of an intersection of the determined first and second lines 31, 35 (step S2e), wherein the calculated 3-D coordinates define point $P_1$ in 3-D space 32.

In other words the desired anatomy 23 lies between x-ray sources 21, 22 and corresponding x-ray detectors 24, 25. The lines 33, 34, 36 and 37 shall give information about the optical path between the x-ray sources 21, 22 and the corresponding x-ray detectors 24, 25. The two x-ray sources 21, 22 and corresponding x-ray detectors 24, 25 are in reality one x-ray source and one x-ray detector of the same C-arm CT, which merely differ in their perspectives of desired anatomy. On the position of the x-ray detector 24 the x-ray projection image 26 from a first perspective is shown, which shall clarify that the x-ray projection image always correlates with a corresponding x-ray source/x-ray detector position, which is gained via a ripple marker 32. In reality, the user selects via HMI (not shown) on which the x-ray projection image 26 is displayed a point/landmark 29. In a next step the calculation unit (not shown) calculates a first line 35 between the point/landmark 29 and the x-ray source 22. In a next step a part of the first line 35, which lies between the lines 33 and 34, is projected on the second x-ray projection image 27. The second x-ray projection image 27 corresponds to the x-ray source 21 and the x-ray detector 25 in the second perspective of the desired anatomy 23. The projected line 30 on the second x-ray projection image 27 serves as constraint, on which the landmark/point 28 can lie, for the user's selection of the landmark/point 28. The two landmarks/points 28, 29 represent the same feature of the desired anatomy only from different perspectives. After the selection of the landmark/point 28 in the second x-ray projection image 27, a line 31 is calculated between the x-ray source 21 and the landmark/point 28. The 3-D coordinates of the landmark/point in 3-D space are derived from the intersection of the lines 31 and 35.

Figure 5:
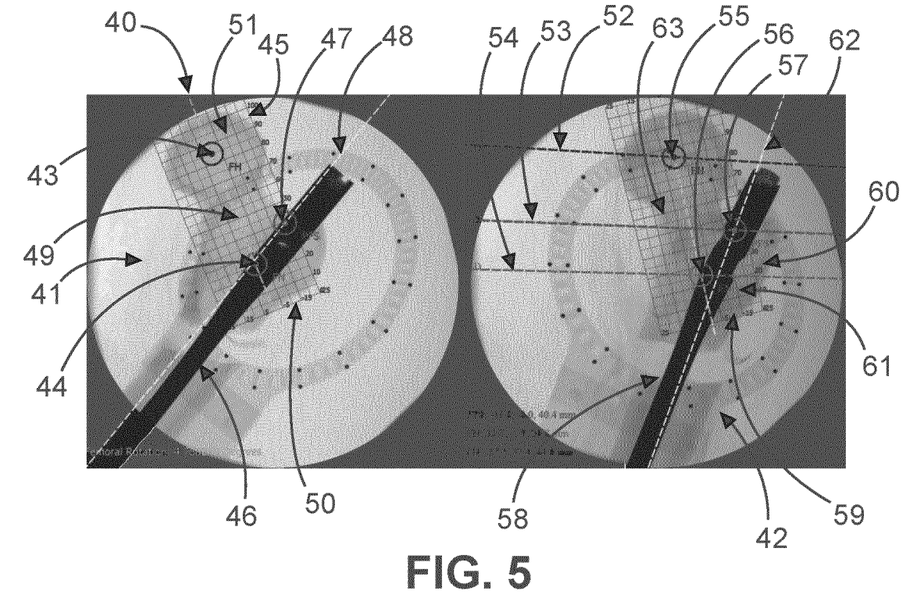
FIG. 5 shows exemplary x-ray projection images with a respectively overlaid scaled virtual grid according to an embodiment.

FIG. 5 shows exemplary a section of x-ray projection images 40 with overlaid scaled virtual. The section of x-ray projection images 40 comprises a first x-ray projection image 41 and a second x-ray projection image 42, which show the same desired object from two different perspectives. The desired object lies respectively below the grid 51, 61. Further an implant 46, 58 with an overlaid orientation line 48, 62 is displayed. Point 43, 55 and point 44, 56 represent the selected points from user input, which define the region interest and are used for the construction of the scale grid. Lines 49, 63 are defined by the points 43, 55 and 44, 56. The scale grid 50 comprises cross lines and longitudinal lines and has millimeter scale in cross direction 50, 59 and longitudinal direction 51, 60. Points 43, 44 and 47 serve also as orientation assistance for the user in second x-ray projection image 42 and represent the top view the orientation lines 54, 53 and 52. As a result it is easier for the user to imagine the change of perspective corresponding x-ray projection images.

Figure 6:
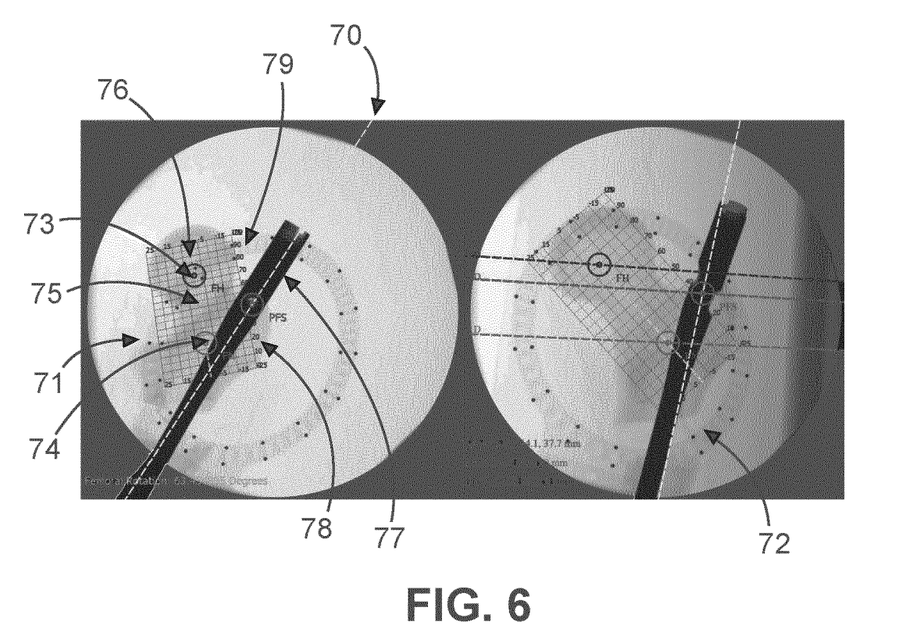
FIG. 6 shows exemplary x-ray projection images with a respectively overlaid scaled virtual grid with a change in magnification of the scale according to an embodiment.

FIG. 6 shows an exemplary section 70 of x-ray projections images 71, 72 with overlaid scaled virtual grids with a change in magnification of the scale. Further an implant is also displayed in both x-ray projections images 71, 72. The grid comprises as above mentioned two points 73, 74 which defines the line 75 and are further used for the scaled grid construction. On the contrary to FIG. 5, grid 76 changes its magnification from the bottom 78 to top 79, which means the grid has no equidistant grid size. This is caused by the selection of the points 73, 74 which are not parallel to the detector (not shown).

Other variations to the disclosed embodiments can be understood and effected by those skilled in the art in practicing the claimed invention, from the study of the drawings, the disclosure, and the appended claims. In the claims the word "comprising" does not exclude other elements or steps and the indefinite article "a" or "an" does not exclude a plurality. A single processor or other unit may fulfill the functions of several items or steps recited in the claims. The mere fact that certain measures are recited in mutually different dependent claims does not indicate that a combination of these measures cannot be used to advantage. A computer program may be stored/distributed on a suitable medium such as an optical storage medium or a solid-state medium supplied together with or as part of other hardware, but may also be distributed in other forms, such as via the Internet or other wired or wireless telecommunication systems. Any reference signs in the claims should not be construed as limiting the scope of the claims.

LIST OF REFERENCE SIGNS

- 10 system
- 11, 21, 22 x-ray source
- 12, 24, 25 x-ray detector
- 13 C-arm
- 14 HMI
- 15 calculation unit
- 20 schematic view of defining one point
- 23 object
- 26, 27, 41, 42, 71, 72 x-ray projection image
- 28, 29, 38, 43, 44, 47, 55, 56, 57, 73, 74 point, landmark, intersection
- 30 projected line
- 31,35 line
- 32 ripple marker
- 33, 34, 36, 37 optic path
- 40, 70 section of x-ray projection images
- 45, 50, 59, 60, 78, 79 scale
- 46, 58, 77 implant
- 48, 62 orientation line implant
- 49, 75 center line
- 51,61,76 grid
- 52, 53, 54 orientation line

The invention claimed is:

1. A method of calculating a scaled virtual grid for x-ray projection images, the method comprising
   providing at least a first co-registered x-ray projection image of an anatomy of a patient and a second co-registered x-ray projection image of the anatomy of the patient,
   defining at least two points of the anatomy in 3-D space and determining 3-D coordinates of the at least two points thereby using the first co-registered x-ray projection image and the second co-registered x-ray projection image,
   calculating the scaled virtual grid based on the determined 3-D coordinates of the at least two points, and
   projecting and displaying the calculated scaled virtual grid to a user on an x-ray projection image.

2. The method according to claim 1, wherein calculating the scaled virtual grid comprises:
   calculating at least two control points on a line connecting the defined at least two points; and
   calculating, for each co-registered image of the at least the first co-registered x-ray projection image and the second co-registered x-ray projection image, cross lines,
   wherein each cross line crosses the line connecting the defined at least two points at a control point of the at least two control points, and
   wherein each cross line is parallel with a detector, with which each co-registered image was captured, and each cross line is perpendicular to the line connecting the defined at least two points.

3. The method according to claim 2, further comprising:
   calculating on each cross line one or more control points,
   wherein the one or more control points define the scaled virtual grid for each co-registered image.

4. The method according to claim 3, further comprising:
   projecting and displaying the scaled virtual grid being defined by the one or more control points on the first co-registered x-ray projection image to the user, and
   projecting and displaying the scaled virtual grid being defined by the one or more control points on the second co-registered x-ray projection image to the user.

5. The method according to claim 3, comprising
   calculating the distance in 3-D space between the at least two points, and
   using the calculated distance to determine the distance between at least two of the one or more of control points.

6. The method according claim 5, further comprising
   displaying the determined distance between the at least two control points together with the one or more control points on the co-registered image to the user.

7. The method according to claim 1,
   wherein the first co-registered x-ray projection image and the second co-registered x-ray projection image show the anatomy of the patient from different perspectives.

8. The method according to claim 1, further comprising:
localizing an x-ray imaging device in six degrees of freedom,
wherein the first co-registered x-ray projection image and the second co-registered x-ray projection image were generated with the x-ray imaging device.

9. The method according claim 8,
wherein the localizing is carried out by at least one of using a Ripple marker, using optical tracking of the x-ray imaging device, using internal encoders of the x-ray imaging device, and/or using other image-based markers.

10. The method according to claim 1,
wherein defining the at least two points of the anatomy in 3-D space comprises:
identifying a first landmark of the anatomy in the first co-registered x-ray projection image,
determining a first line on which the first landmark lays between an x-ray source and an x-ray detector that were used for generating the first co-registered x-ray projection image,
identifying a second landmark of the anatomy in the second co-registered x-ray projection image,
determining a second line on which the second landmark lays between the x-ray source and the x-ray detector that were used for generating the second co-registered x-ray projection image,
calculating 3-D coordinates of an intersection of the determined first line and the determined second line, wherein the calculated 3-D coordinates define a first point of the at least two points in 3-D space,
identifying a third landmark of the anatomy in the first co-registered x-ray projection image,
determining a third line on which the third landmark lays between the x-ray source and the x-ray detector that were used for generating the first co-registered x-ray projection image,
identifying a fourth landmark of the anatomy in the second co-registered x-ray projection image,
determining a fourth line on which the fourth landmark lays between the x-ray source and the x-ray detector that were used for generating the second co-registered x-ray projection image, and
calculating 3-D coordinates of an intersection of the determined third line and the determined fourth line, wherein the calculated 3-D coordinates define a second point of the at least two points in 3-D space.

11. The method according to claim 10, further comprising at least one of:
projecting the determined first line onto the second co-registered x-ray projection image, and
projecting the determined third line onto the second co-registered x-ray projection image.

12. The method according to claim 11,
wherein the projection of at least one of the determined first line and the determined third line is used as a constraint on a Human Machine Interface (HMI), which constrains user input possibilities for identifying a landmark in the second co-registered x-ray projection image on the HMI.

13. Device A device for calculating a scaled virtual grid for x-ray projection images, the device comprising:
a processor configured to:
receive at least a first co-registered x-ray projection image of an anatomy of a patient and a second co-registered x-ray projection image of the anatomy of the patient,
calculate at least two points in the co-registered x-ray projection images and in the anatomy thereby determining 3-D coordinates of the at least two points,
calculate the scaled virtual grid based on the determined 3-D coordinates of the at least two points, and
cause a projection and a displaying of the calculated scaled virtual grid to a user on at least one of the first co-registered x-ray projection image and the second co-registered x-ray projection image.

14. A system for calculating a scaled virtual grid for x-ray projection images, the system comprising
the device according to claim 13, and
a Human Machine Interface configured to display the received first co-registered x-ray projection image and the received second co-registered x-ray projection image, the HMI configured to receive input signals from the user for identifying landmarks in the displayed first co-registered x-ray projection image and the second co-registered x-ray projection image of the anatomy.

15. The system according to claim 14, further comprising:
an x-ray imaging device comprising an x-ray source and an x-ray detector for generating the x-ray projection images.

16. The device according to claim 13, wherein, to define the at least two points of the anatomy in 3-D space, the processor is further configured to:
identify a first landmark of the anatomy in the first co-registered x-ray projection image,
determine a first line on which the first landmark lays between an x-ray source and an x-ray detector that were used for generating the first co-registered x-ray projection image,
identify a second landmark of the anatomy in the second co-registered x-ray projection image,
determine a second line on which the second landmark lays between the x-ray source and the x-ray detector that were used for generating the second co-registered x-ray projection image,
calculate 3-D coordinates of an intersection of the determined first line and the determined second line, wherein the calculated 3-D coordinates define a first point of the at least two points in 3-D space,
identify a third landmark of the anatomy in the first co-registered x-ray projection image,
determine a third line on which the third landmark lays between the x-ray source and the x-ray detector that were used for generating the first co-registered x-ray projection image,
identify a fourth landmark of the anatomy in the second co-registered x-ray projection image,
determine a fourth line on which the fourth landmark lays between the x-ray source and the x-ray detector that were used for generating the second co-registered x-ray projection image, and
calculate 3-D coordinates of an intersection of the determined third line and the determined fourth line, wherein the calculated 3-D coordinates define a second point of the at least two points in 3-D space.

17. The device according to claim 16, wherein at least one of a projection of the determined first line onto the second co-registered x-ray projection image and a projection of the determined third line onto the second co-registered x-ray projection image is used as a constraint on a HMI, which constrains user input possibilities for identifying a landmark in the second co-registered x-ray projection image on the HMI.

18. A non-transitory computer-readable storage medium having stored instructions for calculating a scaled virtual grid for x-ray projection images, the instructions, when executed by a processor, cause the processor to:
- receive at least a first co-registered x-ray projection image of an anatomy of a patient and a second co-registered x-ray projection image of the anatomy of the patient,
- define at least two points of the anatomy in 3-D space and determine 3-D coordinates of the at least two points thereby using the first co-registered x-ray projection image and the second co-registered x-ray projection image,
- calculate the scaled virtual grid based on the determined 3-D coordinates of the at least two points, and
- project and display the calculated scaled virtual grid to a user on an x-ray projection image.

19. The non-transitory computer-readable storage medium according to claim 18, wherein the instructions, when executed by the processor, further cause the processor to: wherein, to define the at least two points of the anatomy in 3-D space, the processor is further configured to:
- identify a first landmark of the anatomy in the first co-registered x-ray projection image,
- determine a first line on which the first landmark lays between an x-ray source and an x-ray detector that were used for generating the first co-registered x-ray projection image,
- identify a second landmark of the anatomy in the second co-registered x-ray projection image,
- determine a second line on which the second landmark lays between the x-ray source and the x-ray detector that were used for generating the second co-registered x-ray projection image,
- calculate 3-D coordinates of an intersection of the determined first line and the determined second line, wherein the calculated 3-D coordinates define a first point of the at least two points in 3-D space,
- identify a third landmark of the anatomy in the first co-registered x-ray projection image,
- determine a third line on which the third landmark lays between the x-ray source and the x-ray detector that were used for generating the first co-registered x-ray projection image,
- identify a fourth landmark of the anatomy in the second co-registered x-ray projection image,
- determine a fourth line on which the fourth landmark lays between the x-ray source and the x-ray detector that were used for generating the second co-registered x-ray projection image, and
- calculate 3-D coordinates of an intersection of the determined third line and the determined fourth line, wherein the calculated 3-D coordinates define a second point of the at least two points in 3-D space.

20. The non-transitory computer-readable storage medium according to claim 19, wherein at least one of a projection of the determined first line onto the second co-registered x-ray projection image and a projection of the determined third line onto the second co-registered x-ray projection image is used as a constraint on a HMI, which constrains user input possibilities for identifying a landmark in the second co-registered x-ray projection image on the HMI.

* * * * *